United States Patent [19]

Ashton et al.

[11] 4,258,130
[45] Mar. 24, 1981

[54] METHOD FOR DETECTION OF ANTIGENS

[75] Inventors: David H. Ashton, Brea; George Tharrington, Jr., Yorba Linda, both of Calif.

[73] Assignee: Hunt-Wesson Foods, Inc., Fullerton, Calif.

[21] Appl. No.: 859,300

[22] Filed: Dec. 12, 1977

[51] Int. Cl.$^3$ ............................................. C12Q 1/66
[52] U.S. Cl. .......................................... 435/7; 424/8; 424/12; 435/34
[58] Field of Search ............. 195/2, 4, 29, 5, 103.5 A, 195/103.5 M; 23/230 B; 424/1, 8, 12; 435/7, 34; 426/231, 232, 233

[56] References Cited

U.S. PATENT DOCUMENTS

| | | | |
|---|---|---|---|
| 3,654,090 | 4/1972 | Schurs | 195/103.5 A |
| 3,966,898 | 6/1976 | Sjöguist et al. | 435/7 |
| 3,992,516 | 11/1976 | Lim | 424/12 X |
| 4,002,532 | 1/1977 | Weltman | 424/12 X |
| 4,067,959 | 1/1978 | Bolz | 424/12 |

OTHER PUBLICATIONS

Reamer, et al., "Increased Sensitivity of Immunofluorescent Assay for Salmonella in Nonfat Dry Milk", *Applied Microbiology*, vol. 18, No. 3, (1969), pp. 328–331.
Thomason, et al., "Evaluation of Commercial Conjugates for Fluorescent Antibody Defection of Salmonellae", *Applied Microbiology*, vol. 27, No. 5, (1974), pp. 862–869.
Silliker et al., "The Fluorescent Antibody Technique as a Means of Detecting Salmonellae in Foods", *J. Food Science*, vol. 31, No. 1 (1966), pp. 240–244.
Tijssen et al., "Basic Techniques in Advanced Immunocyrochemistry Use of Enzymically Active Fab Fragments as Tracers", *Chem. Abst.*, vol. 83, No. 3, p. 228 (1975), abs. No. 24530n.
Kabat, *Structural Concepts in Immunology and Immunochemistry*, Holt, Rinehart and Winston, Inc., New York (1968), pp. 162–167.
Gonatas et al., "I. Demonstration of Intracellular Immunoglobulin with $^{125}$I Fab Antibody Fragments II Segregation and Internalization of Immunoglobulin and of Lactoperoxidase-Iodnated Proteins of Lymphoid Cell Plasma Membranes", *Immunoenzymatic Techniques*, American Elsevier Pub. Co., New York, (1976), pp. 231–245.
Tharrington et al., "Nonspecific Staining of a Lactobacillus by Salmonella Fluorescent Antibodies", *J. Food Science*, vol. 43 (1978), pp. 548–552.

*Primary Examiner*—Thomas G. Wiseman
*Attorney, Agent, or Firm*—Marvin E. Jacobs

[57] ABSTRACT

False positive reactions with fluorescent antibodies such as Lactobacillus reaction with IgG-antiSalmonella are avoided by enzymatic treatment of the IgG to remove the non-antibody, Fc, fragment of the IgG.

9 Claims, No Drawings

METHOD FOR DETECTION OF ANTIGENS

BACKGROUND OF THE INVENTION

1. Field of the Invention

The present invention relates to detection of Salmonella antigens and to a method of treating an antibody to improve specificity of the test.

2. Description of the Prior Art

An immunofluorescent procedure for detection of antigens such as Salmonella in foods and animal by-products is in general use (Silliker, J. H. et al *J. Food Sci* 31: 240–244, 1966). The fluorescent antibody technique is supposed to be specific. However, non-Salmonella antigens of similar rod-like morphology sometimes react with the fluorescent antibody to give a false positive reaction. It has been determined that *Lactobacillus plantarum* strain GT, a harmless rod-like antigen, masquerades as Salmonella by binding to the immunoglobulin G (IgG) and gives false positive reactions in the Salmonella fluorescent antibody detection procedure. It has further been determined that the non-*Salmonella Lactobacillus* binds non-specifically to the non-antibody Fc portion of the IgG molecule.

Antibodies belong to the class of proteins called immunoglobulins. Immunoglobulin gamma (designated IgG) is the predominant antibody in the blood of most higher vertebrates and has been the most intensively studied of the five types of immunoglobulins. It has a molecular weight of about 160,000, which indicates that its molecule consists of some 23,000 atoms.

IgG is made up of four polypeptide chains, each consisting of amino acid units joined by peptide bonds. The four chains are paired so that the molecule consists of two identical halves, each with one "heavy", or long, chain and one "light", or short, chain. The two chains of each pair are cross-linked by covalent bonds between the sulfur atoms of the amino acid cystine. If these disulfide bonds are split, the heavy and light chains will remain bound to one another by noncovalent interactions.

IgG molecules are composed of three parts of about equal size. Two of them are identical and are designated Fab, for "fragment, antigen-binding". The Fab fragments of an IgG molecule each have a combining site. It is because the intact antibody molecule has two such sites that it is able to cross-link antigenic materials into inactive complexes. The third fragment is designated Fc because it crystallizes readily. It does not bind antigen, but it has other important biological activities.

In the currently accepted model of IgG, the heavy and light chains are arranged in the shape of a Y. According to this model, the Fc fragment is the stem of the Y and consists of the lower half of the two heavy polypeptide chains, which are joined together by one interchain disulfide bridge or more. The two Fab fragments are the prongs of the Y, and each consists of one entire light chain and the rest of the heavy chain, with an antigen-combining site of identical specificity at the far end.

SUMMARY OF THE INVENTION

The specificity of the fluorescent antibody detection procedure for an antigen conjugate is improved in accordance with the invention by modifying the IgG molecule to remove the Fc portion that binds non-specifically to morphologically similar micro-organisms. The modification if conducted by enzymatic treatment of the IgG molecule with a proteolytic enzyme capable of cleaving the Fc portion from the molecule. The desired Fab portion is separated and labeled with fluorescent dye. The Fab portion has demonstrated increased specificity for Salmonella and does not bind non-specifically to Lactobacillus.

The invention is applicable to immunoglobulin derived from different animal sources, primarily vertebrates, preferably mammals. Most commercial sources of Salmonella antibody are derived from rabbits. The immunoglobulin is preferably from class G.

The IgG modification method employs a proteolytic enzyme effective in the pH range of 1 to 7. Pepsin has proved most effective since it removes the Fc portion without separating the Fab portion into fragments similar in size to the Fc portion. However, other proteolytic enzymes such as papain may be utilized.

Enzymatic digestion is conducted at a temperature of from 20° C. to about 45° C. for a time effective to split substantially all the Fc fragment from the IgG molecule, usually from 10 to 20 hours. The enzyme-substrate concentration ratio is usually 1/100 to 2/100.

After digestion is complete the Fab fragments are separated from the Fc fragments suitably by chromatographic separation through a column suitably containing solid, particulate polymeric chromotographic medium, such as hydrophilic insoluble molecular sieves. Usually cross-linked polysaccharides such as dextran containing ion-exchange functionality are utilized such as Sephadex. The Fab fragment is eluted first from the column by means of a phosphate buffer (0.2 M NaCl-0.01 M sodium phosphate buffer (pH 8.2) containing 0.002 M EDTA). The Fab fragment is then labeled with an indicatable atom or group of atoms which may be radioactive, and/or coloring and/or fluorescent. Fluorescent groups are readily introduced on the Fab fragments and are readily detected visually or instrumentally.

The fluorescent dye can be attached to the Fab fragment before digestion, after digestion or after separation. Economy of processing dictates the latter course. The dye can be absorbed onto the surface. However, it is preferred to covalently couple a functionally substituted fluorescent dye to the Fab fragment.

The Fab fragment has carboxyl and amine sites which are reactive with sulfonyl chloride, cyanate, isothiocyanate, sulfonic acid, carboxyl, amine and carbonyl chloride groups. Representative functionally substituted fluorescent dyes are Dansyl chloride (sulfonyl chloride of 1-dimethylaminonaphthalene-5-sulfonic acid), Tetramethylrhodamine isothiocyanate (TDIC), Fluorescein isothiocyanate (FITC), Fluorescamine, RB 200 sulfonyl chloride, Fluorescein carbonyl chloride, Aminofluorescein, Ethidium bromide (2,7-diamino-9-phenylphenanthridine-10-ethyl bromide) and the like. The fluorescent dye reaction with IgG is well known in the art and the reaction with separated Fab follows the same procedure of reacting a stoichiometric excess of the dye with the protein in buffer at a pH from 8 to 10 followed by dialysis.

Antigens are detected in food by incubating the food sample in lactose broth followed by selective enrichment in a tetrathionate or selenite cystine broth. An aliquot is exposed to fluorescent antibodies, incubated on a microscope slide, washed and then observed for fluorescence in a fluorescent microscope.

These and many other attendant advantages of the invention will become apparent as the invention becomes better understood by reference to the following detailed description of the invention and examples of practice.

DESCRIPTION OF THE PREFERRED EMBODIMENTS

Example 1

A solution containing 25.2 mg/l of Salmonella IgG sera prepared from rabbits was digested with pepsin (1% by weight based on IgG). The solution was digested at 37° C. for 18 hours. The solution was then chromatographed on a Sephadex G-75 column and eluted with 0.2 M NaCl, 0.01 M sodium phosphate buffer (pH 8.2) containing 0.002 M EDTA. The first eluted Fab containing eluate was labeled with FITC by reacting 0.05 mg FITC/mg Fab in a system containing 3 cc carbonate bicarbonate buffer (0.5 M, pH 9), 10 cc saline (85%) and 2 cc of acetone, cooled in acetone dry ice bath, followed by dialysis in 0.1 M phosphate buffer saline (0.1 M, pH 7.2).

Example 2

(a) 25 g of food sample was incubated in 225 mls of lactose broth at 35° C. for 24 hours.

(b) 1 ml (a) was selectively enriched in 9 mls of tetrathionate at 35° C. for 24 hours.

(c) An aliquot of (b) was exposed to the fluorescent Fab Salmonella sera of Example 1 and incubated for 30 minutes on a microscope slide, and washed. Fluorescence of rod-like Salmonella was observed under a fluorescent microscope.

Example 3

Non-antibody IgG from rabbits was labeled with FITC and demonstrated to strain Lactobacillus plantarum, strain GT.

The latter experiment demonstrates that Lactobacillus non-specifically binds to the Fc fragment of IgG. When Lactobacillus was incubated and exposed to the separated Fab Salmonella sera, no fluorescence was observed.

It is to be realized that only preferred embodiments of the invention have been described and that numerous substitutions, modifications and alterations are permissible without departing from the spirit and scope of the invention as defined in the following claims.

What is claimed is:

1. An improved method of increasing the specificity of detecting Salmonella antigens in a food sample containing non-Salmonella antigens of similar rod-like morphology capable of non-specific binding to the Fc portion of the IgG-anti-Salmonella antibody comprising the steps of:

enzymatically digesting IgG-anti-Salmonella antibody with a proteolytic enzyme to cleave the Fc portion from the Fab portion;

separating the Fab portion from the Fc portion;

labeling the Fab portion with a fluorescent dye;

incubating the food sample in a first broth followed by selective enrichment of the sample in a second broth;

exposing said incubated food sample to the labeled Fab portion; and detecting the presence of Salmonella antigen in the food sample by incubating the exposed food sample, washing the sample and observing the fluorescence of the sample.

2. A method according to claim 1 in which the enzyme is pepsin.

3. A method according to claim 2 in which the enzymatic digestion is conducted at a temperature of 20° C. to 45° C. at a pH of 1–7 and the ratio of enzyme to IgG is from 1/100 to 1/200.

4. A method according to claim 1 in which the Fab portion is separated by chromatography.

5. A method according to claim 4 in which the Fab portion is labeled by coupling reaction with a functionally substituted fluorescent dye.

6. A method according to claim 5 in which the dye is fluorescein isothrocyanate.

7. A method according to claim 1 in which the first broth is a lactose broth and the second broth is a tetrathionate or selenite crystal broth.

8. A method according to claim 7 in which the food sample is incubated in the first broth at 35° C. for 24 hours and the second broth 35° C. for 24 hours.

9. A method according to claim 1 in which said non-Salmonella antigen is lactobacillus.

* * * * *